United States Patent [19]

Monfredo et al.

[11] 4,391,589

[45] Jul. 5, 1983

[54] SURGICAL DENTAL ARTICULATOR

[75] Inventors: Joseph R. Monfredo, San Diego; Ronald H. Roth, San Mateo, both of Calif.

[73] Assignee: Johnson & Johnson Dental Products Company, New Brunswick, N.J.

[21] Appl. No.: 286,449

[22] Filed: Jul. 27, 1981

[51] Int. Cl.³ .................................................. A61C 11/00
[52] U.S. Cl. ...................................... 433/63; 433/55; 433/59
[58] Field of Search .................................... 433/54–67

[56] References Cited

U.S. PATENT DOCUMENTS

| | | | |
|---|---|---|---|
| 198,853 | 1/1878 | Oehlecker | 433/65 |
| 2,613,440 | 10/1952 | Murray et al. | 433/55 |
| 2,765,533 | 10/1956 | McMorris | 433/64 |
| 2,959,857 | 11/1960 | Stoll | 433/55 |
| 3,159,915 | 12/1964 | Beu et al. | 433/57 |
| 3,590,487 | 7/1971 | Guichet | 433/62 |
| 3,815,242 | 6/1974 | Martfay et al. | 433/63 |
| 4,047,302 | 9/1977 | Cheythey | 433/56 |
| 4,058,895 | 11/1977 | Mack et al. | 433/57 |
| 4,083,114 | 4/1978 | Acevedo | 433/63 |
| 4,128,942 | 12/1978 | Schleich | 433/60 |
| 4,163,319 | 8/1979 | Ouaknine | 433/60 |
| 4,185,387 | 1/1980 | Weber | 433/61 |

FOREIGN PATENT DOCUMENTS

| | | | |
|---|---|---|---|
| 2440731 | 7/1980 | France | 433/60 |
| 596232 | 12/1947 | United Kingdom | 433/62 |

*Primary Examiner*—John J. Wilson
*Attorney, Agent, or Firm*—Townsend and Townsend

[57] ABSTRACT

A surgical dental articulator having a pivotable frame to which a pair of independently adjustable cantilevers carrying opposed dental casts are mounted. The dental casts are mounted to the cantilever for movement along the cantilever axis and for pivotal movement about a first pivot axis normal to the cantilever axis. The cantilevers are each mounted to the frame by a cantilever support assembly which includes linear support and pivot assemblies. The linear support assembly includes a first transverse support fixedly mounted to the frame and defining a first linear path and a second transverse support slidably mounted to the first transverse support for movement parallel to the first linear path and defining a second linear path perpendicular to the first linear path. The pivot assembly is slidably mounted to the second linear support along the second linear path via a pair of pivot arms. The cantilever is pivotably mounted to the pivot assembly for rotation about the cantilever axis and about a second pivot axis perpendicular to the longitudinal axis. The upper and lower dental casts can be individually moved along three separate, nominally orthogonal linear paths and about three separate, nominally orthogonal pivot axes. The cast mounting assemblies have scales marked directly thereon so that movement of the dental casts can be measured directly from the articulator.

8 Claims, 7 Drawing Figures

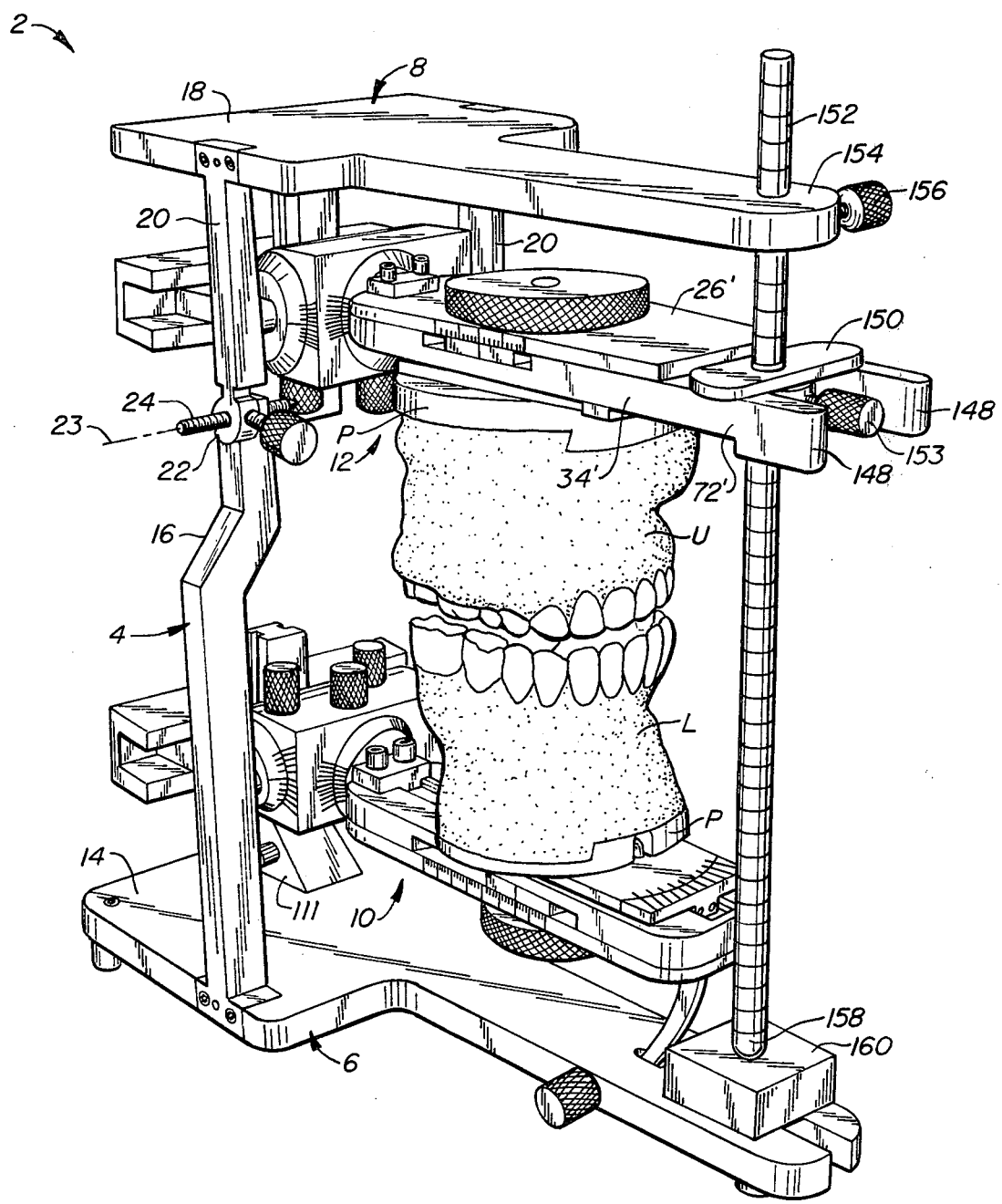
FIG._1.

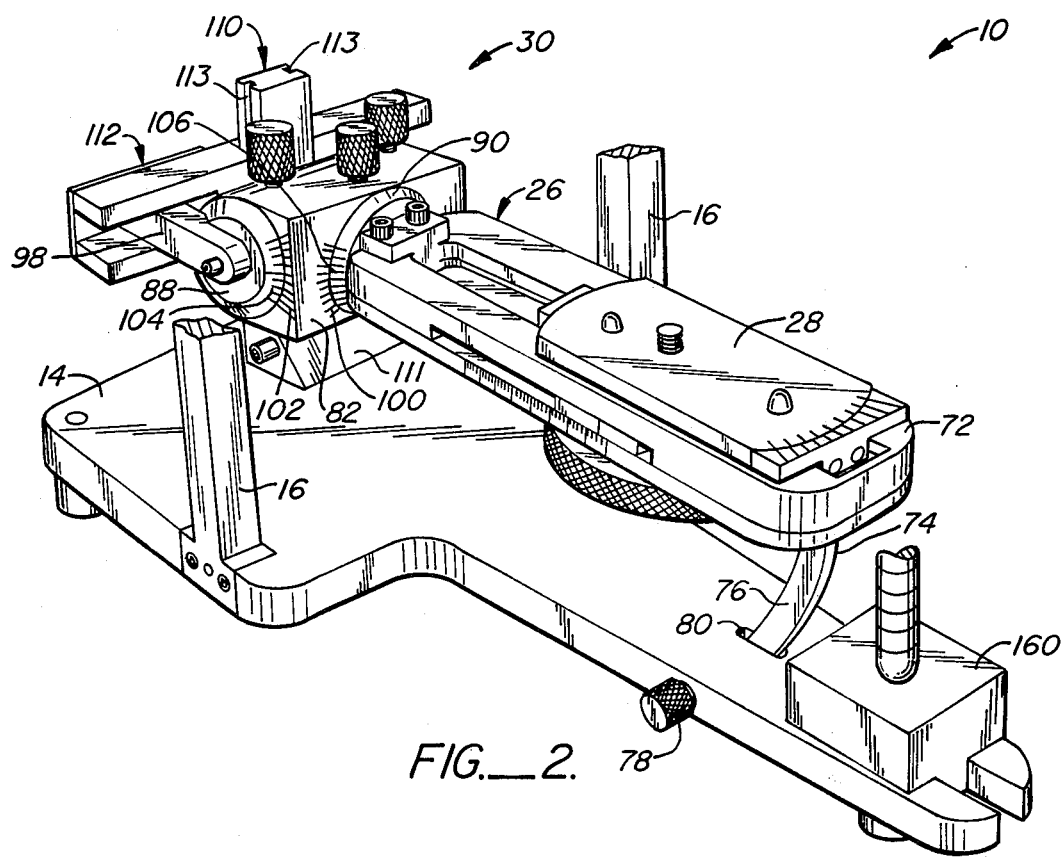
FIG._2.
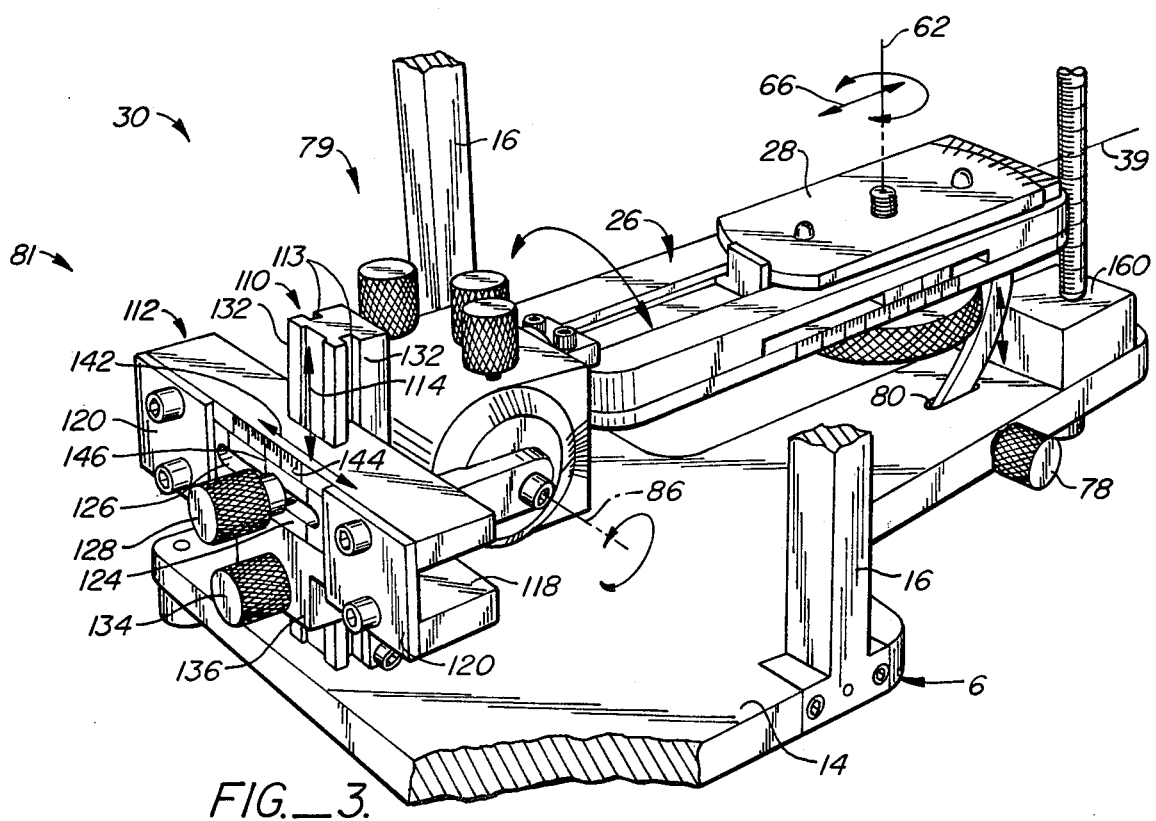
FIG._3.

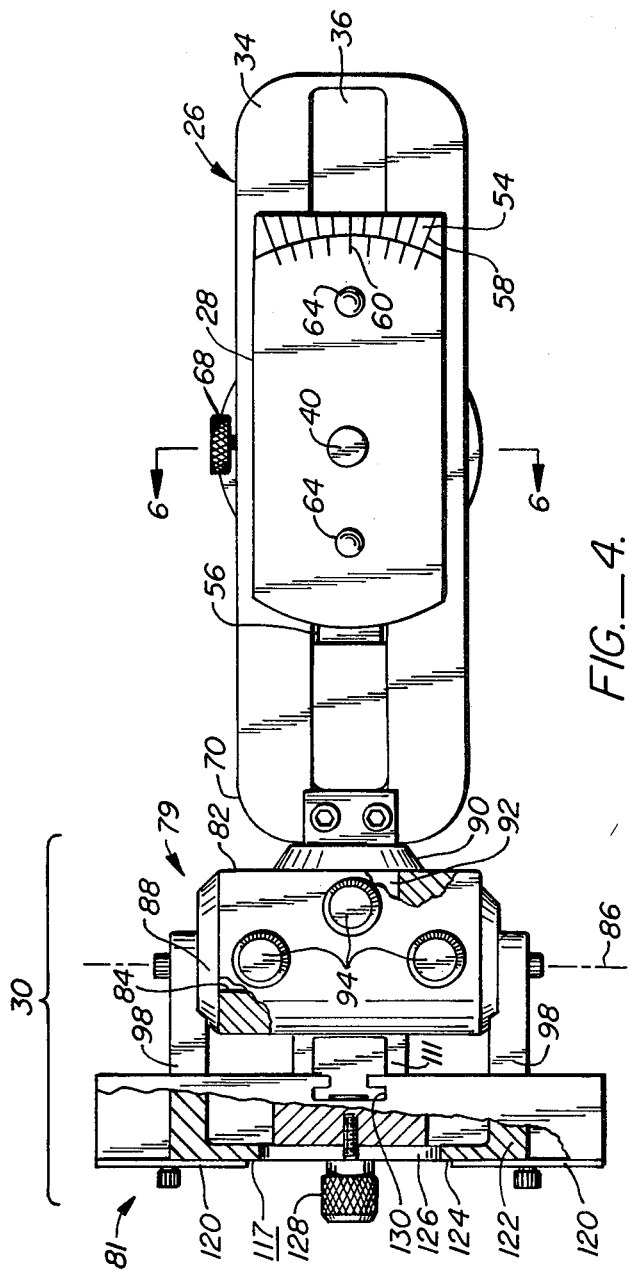
FIG._4.
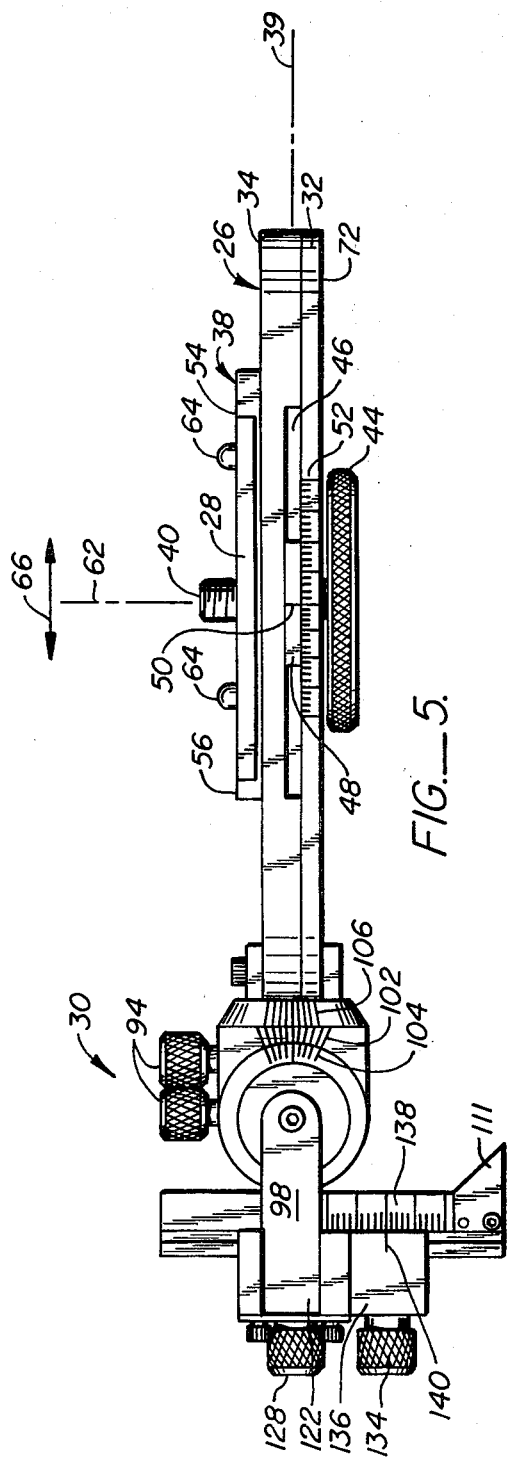
FIG._5.

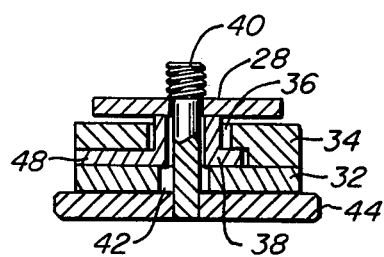
FIG._6.
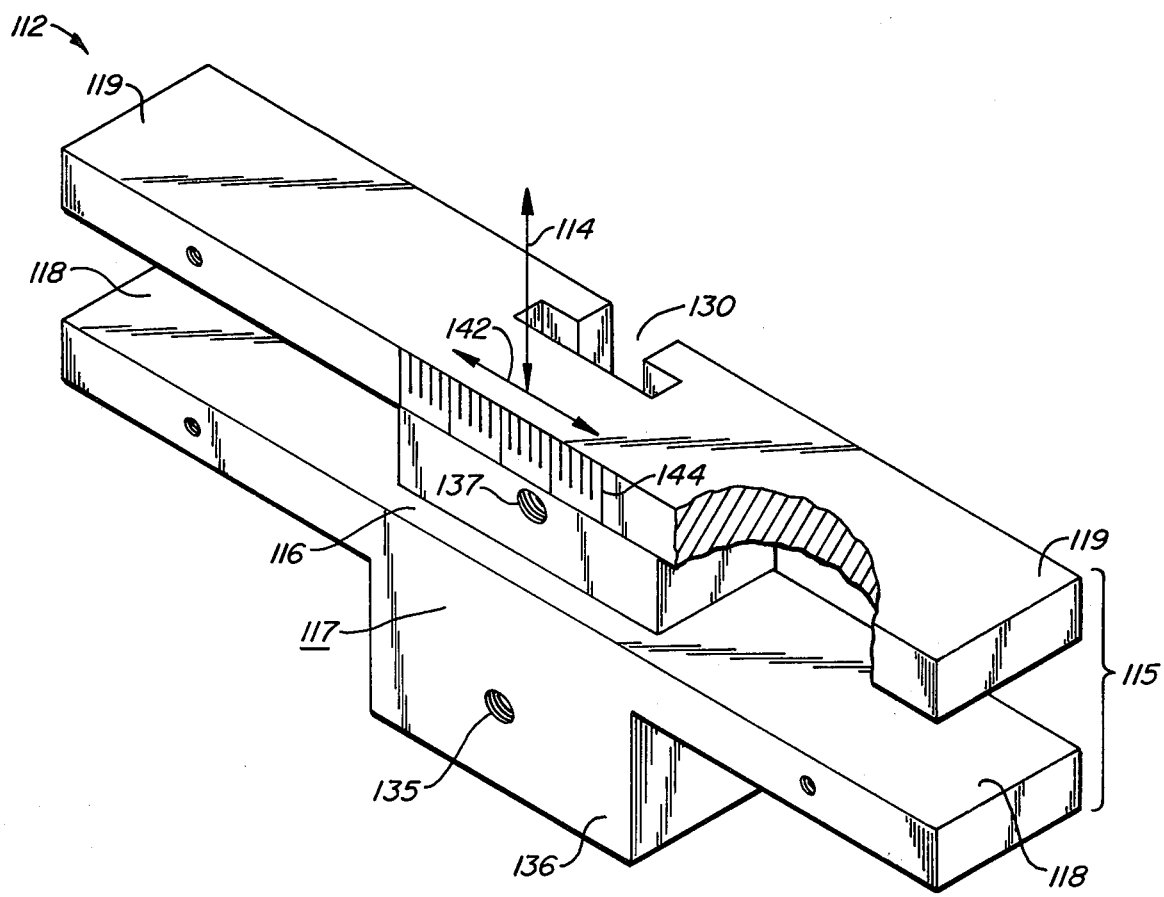
FIG._7.

SURGICAL DENTAL ARTICULATOR

BACKGROUND OF THE INVENTION

For numerous orthodontic procedures casts are made of the teeth from both the upper and lower jaws. These dental casts are then mounted to a mounting plate which is attached to a dental articulator to reproduce the location and movement of the upper teeth and maxilla, relative to the lower jaw, and mandibular teeth. Many of these prior art articulators are used in making artificial dentures and inlays or crowns and are known as gnathological articulators. Other articulators are used in oral surgery during which, typically, sections of bone or other tissue are removed to alter or shift the relative relation between the upper and lower jaws.

In many of the prior art articulators the lower jaw remains fixed and cannot be moved relative to the hinge axis of the articulator; see U.S. Pat. Nos. 3,159,915; 3,590,487; 4,058,895 and 4,185,387. This is a disadvantage since the true operable relationship between the jaws cannot be accurately modeled for surgical techniques in which the lower jaw is altered in size and shape.

Other prior art articulators attempt to simulate the rather complicated movements of a human mandibular joint. This type of gnathological articulator allows the user to view the interplay between artificial teeth so that appropriate adjustments can be made. See, for example, U.S. Pat. No. 4,047,302. Other related devices are directed to apparatus for the measurement and recording of jaw movement, see U.S. Pat. No. 3,815,242, and are used in fabricating dentures, bridges and the like.

Some of the prior art articulators have recognized the importance of being able to independently move both the upper and lower dental casts. However, they typically do not provide all six degrees of freedom, three translational and three rotational, for both dental casts. If all six degrees of freedom are provided, then the three rotational degrees of freedeom are generally provided via a universal or ball joint; the individual rotational movements about three orthogonal rotational axes are therefore not directly readable from the apparatus. See U.S. Pat. Nos. 4,083,114; 4,128,942. Another patent which may be of interest is U.S. Pat. No. 2,959,857.

An exemplary surgical procedure using a prior art surgical dental articulator is a mandibular advancement. Before the surgery, a surgical splint, which is a U-shaped piece of plastic material, must be constructed for placement between the patient's upper and lower dental arches after the surgery. This splint is used to properly position the lower jaw to the upper jaw which are wired together via the teeth while the bone tissue heals.

Preparatory to making the splint, the patient's dental casts are mounted to an articulator, such as the articulator made by SAM of Munchen, West Germany. For lower jaw surgery, the articulator is held in a protrusive or retrusive position to construct the splint.

For upper jaw surgery, the base of the plaster cast is made quite thick so that a pattern of grid lines can be etched on the base of the cast to serve as a reference. The amount of bone to be removed from the patient is determined from head X-rays using standard techniques. For example, assume that 7 mm of bone is to be removed from the posterior or rear portion of the upper jaw and 4 mm from the anterior or front portion of the upper jaw. Using the etched grid lines as a guide, a wedge of material 7 mm at the rear of the cast and 4 mm thick at the front of the cast is removed from the base of the upper plaster dental cast. This is typically accomplished using a hand saw or a circular cutter. The separated portions of the dental cast are then joined back together using a thin mix of mounting plaster and the dental casting is remounted on the articulator.

The pliant U-shaped splint material is placed between the teeth of the dental casts and impressions of the occlusal surfaces of the teeth are formed in the splint material. The splint material can be an acrylic in which a monomer and a polymer are mixed to produce a plastic, dough-like material which is formed into the U-shape. The splint material is hardened by placing it, while still between the teeth of the dental casts on the articulator, in a proper environment for the particular material used. One type is cured or hardened by placing in a warm, pressurized environment.

After the removal of the wedge of material, the teeth on the articulator should be in the same relative position as the teeth of the patient after the removal of the bone. If this is so, the indentations in the surgical splint created by the teeth of the plaster dental casts will be identically positioned as the patient's teeth will be after surgery. This is important because patient's jaws are wired shut for several weeks or months while healing.

Two basic shortcomings exist with the above-described procedure. First, if one uses an articulator in which the lower dental cast is fixed, the upper dental cast must be moved even though the lower jaw is the one on which the surgery is performed. Therefore the positions of the dental casts relative to the hinge axis will not be correct. Second, the procedure for scoring grid lines on the mounting plaster on the base of the dental cast, plotting the tissue to be removed, removing sections from the base of the dental cast, and then bonding the severed sections of the dental cast back together is time consuming and cumbersome.

Therefore, what has been missing in the prior art is a surgical articulator which can be used by the orthodontist or oral surgeon to independently move either or both of the dental casts a measured amount in any individual translational or rotational direction in each plane of space.

SUMMARY OF THE INVENTION

A surgical dental articulator is disclosed having independently moveable upper and lower dental cast mounting assemblies attached to a frame. The frame includes an upper support and a base which are coupled at a pivotal hinge axis corresponding to the terminal hinge axis of a patient. The upper and lower dental cast mounting assemblies are mounted to the upper support and base respectively. The dental cast mounting assemblies each include a cantilever, which carries a cast mount upon which a respective dental cast is mounted, and a cantilever support assembly. Each dental cast mount is movable in a longitudinal direction parallel to the axis of the cantilever and can pivot about a first pivot axis for rotary displacement of the dental casts. The opposed cantilevers are mounted to the frame by a cantilever support assembly.

Each cantilever support assembly includes first and second transverse supports and a pivot assembly. The first transverse support is fixedly mounted to the frame and defines a first linear path. The second transverse support is slidably mounted to the first transverse support for movement along the first support parallel to the first linear path. The second transverse support defines a second linear path perpendicular to the first linear path. The pivot assembly is slidably mounted to the second linear support via a pair of pivot arms for movement along the second linear path.

One end of the cantilever is pivotably mounted to the pivot assembly for rotation of the cantilever about its longitudinal axis. The pivot assembly also permits the cantilever to pivot in a generally vertical plane about a second pivot axis passing through the outer ends of the pivot arms.

Each dental cast is mounted via a mounting plate to the cast mount on the cantilever. The upper and lower dental casts can be individually moved along separate, nominally orthogonal linear paths and about separate, nominally orthogonal pivot axes. The term "nominally orthogonal," as used in this application, is defined below. The cast mounting assemblies have individual scales for each of the three linear movements and for each of the three pivotal movements. The scales are marked directly on the articulator so that any movements are readable directly from the articulator.

The surgical articulator of the present invention enables the user to separately adjust the position and orientation of either of the dental casts along three nominally orthogonal paths and about three nominally orthogonal axes thus providing each dental cast with six independent degrees of freedom. This ensures that precisely the desired relationship between the two dental casts can be achieved and that movement of the casts is readable on the six independent measuring scales for each cast mounting assembly. The proper relationship between the jaws, and also between the jaws and the hinge axis, is therefore maintained.

Since the lateral and angular distances are indicated on the apparatus, the user can accurately reposition dental casts without the need for measures such as cutting out sections of the dental casts when making surgical splints. No blocking off of the bases of the dental casts into grid squares, scribing the section to be removed and sawing the casts into sections to remove material is required. The user need merely move the appropriate dental cast along one or more of the linear paths or around one or more of the pivotal axes, or both, to achieve the desired relationship. Time is saved and accuracy is enhanced.

Thus, the user can accurately and simply position the dental casts relative to each other, to the hinge axis, or to both, through the use of the individual measuring scales provided for each of the three linear paths and for each of the three pivot axes.

When surgical splints are made, the plastic splint material is placed between the upper and lower occlusal surfaces and the dental casts are pressed together to make the tooth impressions. To reduce the torque on the pivot assembly about the second pivot axis, the upper and lower cantilevers are provided supports at their outer ends. The lower cantilever is supported at its outer end against downward motion and the upper cantilever is supported at its outer end against upward motion, thus resisting the forces exerted on the cantilever support assembly during compression of the splint material.

Other features and advantages of the present invention will become apparent from the following description in which the preferred embodiment has been set forth in detail in conjunction with the accompanying drawings.

BRIEF DESCRIPTION OF THE DRAWINGS

FIG. 1 is a perspective view of the articulator of the present invention showing upper and lower dental casts mounted to casting mounts on the upper and lower cantilevers.

FIGS. 2 and 3 are perspective views of the lower cast mounting assembly mounted to the base portion of the frame.

FIG. 4 is a top view of the lower cast mounting assembly with portions broken away for clarity of understanding.

FIG. 5 is a side view of the lower cast mounting assembly.

FIG. 6 is a sectional view taken along line 6—6 of FIG. 4.

FIG. 7 is an enlarged isometric view of the second linear support.

DETAILED DESCRIPTION OF THE PREFERRED EMBODIMENT

Turning now to FIG. 1, the surgical articulator 2 of the present invention is seen to broadly comprise a frame 4, which includes a base 6 pivotally connected to an upper support 8, a lower cast mounting assembly 10 mounted on base 6 and an upper cast mounting assembly 12 mounted to upper support 8.

Upper and lower cast mounting assemblies 12, 10 are generally identical except for the attitude at which they are mounted to upper support 8 and base 6. Therefore, assemblies 10, 12 will be described in terms of lower assembly 10 recognizing that assembly 12 is of like construction.

Base 6 includes a paddle-shaped plate 14 on which a pair of upright supports 16 extend. Upper support 8 includes a generally horizontal paddle-shaped plate 18 and a pair of depending arms 20. Supports 16 and arms 20 are pivotally joined at a hinge 22. A hinge axis 23 of hinge 22 is defined by a pair of hinge pins 24, the outer end of which are hollow for transfer of measurements from a standard face bow when mounting upper and lower dental casts U, L to mounting assemblies 12, 10 via mounting plates P. Hinge axis 23 corresponds to the terminal hinge axis of a patient.

Turning now to FIGS. 2 and 3, mounting assembly 10 will be described in more detail. Mounting assembly 10 includes generally an elongate cantilever 26 to which a generally planar cast mounting 28 is secured, and a cantilever support assembly 30 fixedly mounted to plate 14 and from which cantilever 26 extends.

With reference also to FIGS. 4–6, cantilever 26 and cast mount 28 will be described first with the description of support assembly 30 to follow. Cantilever 26 includes lower and upper plates 32, 34. Upper plate 34 has a T-slot 36 formed therein along substantially its entire length. A T-bar 38 is mounted within slot 36 for movement parallel to an axis 39 of cantilever 26. Cast mount 28 is pivotally mounted to the top of T-bar 38 about a shaft 40. Shaft 40 extends through lower and upper plates 32, 34 through T-slot 36 and upper plate 34, a hole in T-bar 38 and a longitudinal slot 42 within lower plate 32. Shaft 40 is fixed to a knurled knob 44 beneath lower plate 32. Thus, knob 44, T-bar 38 and cast mounting 28 therewith can be moved parallel to axis 39 of cantilever 26. The amount of movement depends generally on the length of slots 36 and 42.

Upper plate 34 also includes a lateral opening 46 within which a lateral extension 48 of T-bar 38 is located. Extension 48 has a scribe mark 50 for alignment with a scale 52 on lower plate 32. Scale 52 and mark 50 are used to determine the lateral placement of dental cast L along cantilever 26.

T-bar 38 includes a forward extension 54 and a rear extension 56. Extensions 54, 56 and mounting 28 are configured so that mounting 28 can rotate freely between extensions 54, 56. Extension 54 has a first pivot scale 58 marked thereon and mounting 28 has a vernier scale 60 etched adjacent scale 58 for the measurement of the pivotal position of cast mount 28 and dental cast L thereon about a first pivot axis 62 defined by shaft 40. Mount 28 also includes a pair of alignment pins 64 for engagement with appropriately spaced apertures on mounting plate P to which dental cast L is mounted.

Dental cast L is thus provided with lateral movement parallel to axis 39 of cantilever 26 along a first linear path 66 and about first pivot axis 62, axis 62 perpendicular to path 66. Once the desired position of the dental cast is achieved, dental cast L is locked into place along path 66 by the use of a thumb screw 68, which engages T-bar 38. Dental cast L is pivotally fixed relative to axis 62 by tightening knob 44 causing plate P to press against cast mounting 28 which in turn is drawn against T-bar 38 and thus against lower plate 32 of cantilever 26.

Cantilever 26 is supported at its inner end 70 by cantilever support assembly 30 and at its outer end 72 by an adjustable support 74. Support 74, as seen in FIG. 2, includes a curved bar 76 selectively positioned by a knob 78, bar 76 passing through an aperture 80 in plate 14. Support 74 is used merely to reduce the torsion forces on assembly 30.

Cantilever support assembly 30 includes generally a pivot assembly 79 and a linear support assembly 81. Assembly 79, as seen in FIG. 4, includes a housing 82 having a longitudinal aperture 84 defining a second pivot axis 86 and along which a pivot shaft 88 is mounted. A pivot mount 90 secures inner end 70 of cantilever 26 to housing 82. Mount 90 includes a circular shaft portion 92 mounted within a corresponding aperture within housing 82. Knurled knobs 94 are threadably mounted to housing 82 to selectively secure pivot shaft 88 and shaft portion 92 within housing 82. Thus the user can pivot cantilever 26 and lower dental cast L therewith about axis 39 of cantilever 26, first pivot axis 62 and second pivot axis 86. It should be noted that the three pivot axes, longitudinal axis 39, first pivot axis 62 and second pivot axis 86, are nominally orthogonal, that is, they are orthogonal when mounting assembly is as illustrated in the figures with cantilever 26 parallel to plate 14. However, first and second axes 62, 86 do not remain orthogonal when cantilever 26 is pivoted about longitudinal axis 39. Accordingly, the term nominally orthogonal, as used in this application, will refer to directions or axes which are orthogonal in the standard or zeroed position shown in the figures.

As seen best in FIG. 2, housing 82 includes a longitudinal pivot axis scale 100 and a second pivot axis scale 102. Pivot shaft 88 and pivot mount 90 include venier alignment scales 104, 106 for measurement of the amount of rotary movement about second pivot axis 86 and longitudinal axis 39 respectively. Thus, articulator 2 as described thus far provides the user with the ability to pivot the cantilever and supported dental cast in directly measured amounts about three nominally orthogonal pivot axes and along one linear path. The linear support assembly 81, described below, provides the articulator with the final two linear paths.

Linear support assembly 81 includes a first linear support 110, rigidly attached to plate 14 by a triangular block 111 and extending upwardly therefrom, and a second linear support 112 slidably mounted to support 110 for movement parallel to a first linear path 114. A pair of slots 113 are formed along edge 132 of support 110 for engagement with second linear support 112 as described in more detail below.

Support 112, shown best in FIG. 7, is a T-shaped member having a vertically extending T-slot 130 sized for mating engagement with support 110. Support 112 is secured to support 110 at various points along path 114 by a knurled locking knob 134 passing through a threaded hole 135 in a stem portion 136 of support 112. A top portion 115 has a slot 116 along surface 117 opposite and perpendicular to T-slot 130. Portion 115 also has a pair of transverse slots 118 perpendicular to slot 116 and slot 130 at the ends 119 of portion 115. Slots 116, 118 provide a path for movement of pivot assembly 79 therealong as described below.

The inner ends 122 of pivot arms 98, see FIGS. 3 and 4, are joined by a generally thin connecting member 124 having a slot 126 formed therein. Inner ends 122 and member 124, supporting pivot assembly 79 and cantilever 26, are thus slidably supported within slots 116, 118 of support 112. A pair of plates 120 are fixed to surface 117 adjacent ends 119 of top portion 115 to retain inner ends 122 of arms 98 and member 124 within slots 116, 118. A threaded clamping pin 128 threadably engages threaded hole 137 to secure connecting member 124, and thus arms 98, to support 112.

The displacement of second linear support 112 parallel to first linear path 114 is measured using a first linear scale 138, seen best at FIG. 5, with a scribe mark 140 on portion 136 of support 112. Movement of pivot arms 98, and therefore pivot assembly 79 and cantilever 26, within slots 118 parallel to slot 116 and thus parallel to a second linear path 142, is measured using a second linear scale 144 marked on surface 117 of support 112 and a scribe mark 146 on connecting member 124.

The three linear paths 66, 114 and 142 described above are nominally orthogonal as that term has been defined above. When cantilever 26 is pivoted about second pivot axis 86, longitudinal axis 39 and path 66 are no longer perpendicular to first and second paths 114, 142. Complete orthogonality of the three linear paths can be provided by slideably mounting first linear support 110 to plate 14 along a path parallel to longitudinal path 66.

Mounting assembly 12 is nearly identical to assembly 10 and is mounted to upper support to overlie casting mounting assembly 10. Plate 34' of assembly 12 has a pair of longitudinally extending members 148 at outer end 72' of cantilever 26'. Members 148 engage the lower surface of an adjustable stop 150 slidably mounted on a guide pin 152 and fixed in place by a locking screw 153. Guide pin 152 is secured to the tip 154 of plate 18 by a screw 156. The lower end 158 of guide pin 152 rests on a table 160 and supports upper support 8 at an appropriate angular attitude. Stop 150 acts in a similar manner as support 74 by supporting the outer end of the cantilever to reduce the forces which must be resisted by pivot assembly 79 when a surgical splint is being formed between upper and lower casts U, L.

Having thus described the apparatus of the invention, its operation will be described briefly. The user takes the upper and lower dental casts U, L mounted to their respective mounting plates P and mounts each to cast mount 28 by threadably engaging shaft 40. Using a face bow to engage hinge pins 24, the dental casts are positioned relative to hinge axis 23 and each other corresponding to the measurements from the patient. The dental casts can be individually positioned about longitudinal axis 39, first pivot axis 62 and second pivot axis 86 as well as parallel to the three nominally orthogonal paths 66, 114 and 142.

If a surgical splint is to be made between the occlusal surfaces of the teeth on the dental casts, stop 150 is placed above members 148 as shown in FIG. 1. Adjustable support 74 is also adjusted to support outer ends 72 of cantilever 26. Based upon known methods, such as head X-rays, the amount of tissue to be removed or other adjustments to be made to the facial structure are determined. These adjustments determine the shift in the location of one or both of the jaws during the surgery. These shifts are provided by moving the dental casts about one or more of the nominally orthogonal pivot axes and parallel to one or more of the nominally orthogonal linear paths. The amount of movement is read directly from the appropriate scales on the articulator. After the shifts in position are made, a splint can be made by placing the splint material between the occlusal surfaces of the teeth and pressing the teeth of the upper and lower dental casts into the plastic, dough-like splint material. The splint material is cured or hardened to make the impressions permanent. During the surgery, the patient's jaw can be wired shut with the splint between them to ensure that the tissues heal with the jaws properly located.

The surgical dental articulator has been described and its use primarily with respect to a mandibular advancement and maxillary Lefort I procedures. However, it should be understood that the articulator is suited for making splints for other surgical procedures. It is also useful in making functional appliances or activators.

Modification and variations can be made to the disclosed embodiment without departing from the subject of the invention as defined in the following claims.

What is claimed is:

1. A surgical dental articulator for manipulating a set of dental casts, each said dental cast mounted to a mounting plate, comprising:
   a frame having frame sections hingedly attached along a hinge axis, said hinge axis corresponding to the terminal hinge axis of a patient; and
   a pair of means for mounting one said mounting plate and dental cast therewith to each of said frame sections, said mounting means including:
   means for individually and measurably translating said dental casts parallel to three separate, nominally orthogonal paths, said translating means including linear graduated scales so that individual distances translated along said three paths can be read directly;
   means for individually and measureably pivoting said dental casts about three separate, nominally orthogonal pivot axes, said pivoting means including angular graduated scales so that individual angles pivoted about said three pivot axes can be read directly; and
   a first support rigidly mounted to one of said frame sections and along which a second support mounted perpendicular to said first support moves along a first path of said three paths to carry one said dental cast parallel to said first path, said second support defining a second path of said three paths for movement of one said dental cast parallel to said second path;
   whereby the dental casts can be individually and measureably translated along three separate linear paths and pivoted around three separate rotational axes.

2. The articulator of claim 1 wherein:
   said mounting means includes a pivot portion mounted to said second support for movement along said second path and for selectively pivoting said dental cast around first and second axes of said three axes, said first axis perpendicular to said second axis.

3. A surgical dental articulator for manipulating a set of dental casts, each said dental cast mounted to a mounting plate, comprising:
   a frame having frame sections hingedly attached along a hinge axis, said hinge axis corresponding to the terminal hinge axis of a patient; and
   a pair of means for mounting one said mounting plate and dental cast therewith to each of said frame sections, said mounting means including:
   means for individually and measurably translating said dental casts parallel to three separate, nominally orthogonal paths, said translating means including linear graduated scales so that individual distances translated along said three paths can be read directly;
   means for individually and measurably pivoting said dental casts about three separate, nominally orthogonal pivot axes, said pivoting means including angular graduated scales so that individual angles pivoted about said three pivot axes can be read directly;
   a first support rigidly mounted to one said frame section and along which a second support mounted perpendicular to said first support moves along a first path of said three paths to carry one said dental cast parallel to said first path, said second support defining a second path of said three paths for movement of one said dental cast parallel to said second path;
   a pivot portion mounted to said second support for movement along said second path and for selectively pivoting said dental cast around first and second axes of said three axes, said first axis perpendicular to said second axis; and
   a cantilever mounted to said pivot portion and extending therefrom, said cantilever having a longitudinal axis defining a third of said three nominally orthogonal paths, said mounting plate and dental cast therewith mounted to said cantilever for linear movement parallel to said third path and for pivotal movement about a third of said three axes, said third axis perpendicular to said third path;
   whereby the dental casts can be individually and measureably translated along three separate linear paths and pivoted around three separate rotational axes.

4. A surgical dental articulator for mounting a first dental cast in movable, adjustable relationship with respect to a second dental cast comprising:

a frame, said frame having sections pivotally attached at a hinge axis, said hinge axis corresponding to the terminal hinge axis on a patient; and means for mounting the first dental cast to one said frame section, said first dental cast mounting means comprising:

a first linear support mounted to one said frame section;

a second linear support mounted to said first linear support for movement along a first linear path;

a cantilever having inner and outer ends and a longitudinal axis;

means for pivotally mounting said first dental cast to said cantilever about a first axis, said first axis perpendicular to said longitudinal axis;

means for adjustably attaching said first dental cast mounting means to said cantilever for movement along a third linear path parallel to said longitudinal axis;

a pivot assembly mounted to said second linear support for movement of said pivot assembly along a second linear path perpendicular to said first linear path;

said pivot assembly including means for pivotally mounting said cantilever at said inner end to said pivot assembly for pivotal movement of said cantilever about said longitudinal axis; and said pivot assembly including means for selectively pivoting said cantilever about a second axis, said second axis perpendicular to said longitudinal axis;

means for measuring movement of the first dental cast along said first, second and third linear paths and including a separate linear distance scale for each of said three linear paths; and means for measuring movement of the first dental cast about said first, second and longitudinal axes and including a separate angular displacement scale for each of said three axes.

5. The articulator of claim 4 including an adjustable outer end cantilever support mounted to said frame for arresting pivotal movement of said cantilever about said second axis thereby reducing the stresses on said pivot assembly during use.

6. A surgical dental articulator for mounting a first dental cast in movable, adjustable relationship with respect to a second dental cast comprising:

a frame, said frame having frame sections pivotally attached at a hinge axis corresponding to the terminal hinge axis on a patient; and means for mounting the first dental cast to one said frame section, said first dental cast mounting means comprising:

means for measurably mounting the first dental cast for linear movement along three nominally orthogonal linear paths and including a separate linear distance scale for each of said three linear paths;

means for measurably mounting the first dental cast for pivotal movement about three nominally orthogonal axes and including a separate angular displacement scale for each of said three axes;

a first linear support mounted to said one frame section;

a second linear support mounted to said first linear support for movement along a first linear path;

a cantilever having inner and outer ends and a longitudinal axis;

means for pivotally mounting, about a first axis, said first dental cast to said cantilever, said first axis perpendicular to said longitudinal axis;

means for adjustably attaching said last mentioned mounting means to said cantilever for movement along a third linear path parallel to said longitudinal axis;

a pivot assembly mounted to said second linear support for movement of said pivot assembly along a second linear path perpendicular to said first linear path; and said pivot assembly including means for pivotally mounting said inner end of said cantilever thereto for pivotal movement of said cantilever about said longitudinal axis and about a second axis, said second axis perpendicular to said longitudinal axis.

7. A surgical dental articulator for mounting a first dental cast in movable, adjustable relationship with respect to a second dental cast comprising:

a frame, said frame having frame sections pivotally attached at a hinge axis, said hinge axis corresponding to the terminal hinge axis on a patient; and means for mounting the first dental cast to one said frame section, said first dental cast mounting means comprising:

a cantilever having inner and outer ends and a longitudinal axis;

means for mounting the first dental cast for linear movement along three nominally orthogonal linear paths; and means for mounting the first dental cast for pivotal movement about a first, a second and said longitudinal axes, said first, second and longitudinal axes being nominally orthogonal axes;

said linear movement mounting means including means for pivotally mounting said first dental cast to said cantilever for movement about said first axis, said first axis perpendicular to said longitudinal axis, and means for adjustably attaching said first dental cast mounting means to said cantilever for movement along a third linear path parallel to said longitudinal axis.

8. The articulator of claim 7 wherein said first dental cast mounting means further comprises a linear displacement scale for each of said three paths and an angular displacement scale for each of said three axes.

* * * * *